United States Patent
McNeff et al.

(10) Patent No.: US 10,695,393 B2
(45) Date of Patent: Jun. 30, 2020

(54) COMPOSITIONS AND METHODS FOR MITIGATING METHANOGENESIS IN ANIMALS

(71) Applicant: SarTec Corporation, Anoka, MN (US)

(72) Inventors: Larry C. McNeff, Anoka, MN (US); Clayton V. McNeff, Andover, MN (US)

(73) Assignee: SarTec Corporation, Anoka, MN (US)

(*) Notice: Subject to any disclaimer, the term of this patent is extended or adjusted under 35 U.S.C. 154(b) by 16 days.

(21) Appl. No.: 15/978,397

(22) Filed: May 14, 2018

(65) Prior Publication Data

US 2018/0333450 A1 Nov. 22, 2018

Related U.S. Application Data

(60) Provisional application No. 62/506,726, filed on May 16, 2017.

(51) Int. Cl.

| | | |
|---|---|---|
| *A23K 20/121* | (2016.01) | |
| *A61K 36/886* | (2006.01) | |
| *A61K 36/8965* | (2006.01) | |
| *A61K 36/752* | (2006.01) | |
| *A61K 36/48* | (2006.01) | |
| *A61K 36/898* | (2006.01) | |
| *A23K 20/158* | (2016.01) | |
| *A61K 36/77* | (2006.01) | |
| *A61K 31/20* | (2006.01) | |
| *A61K 31/215* | (2006.01) | |
| *A61P 31/04* | (2006.01) | |
| *A23K 20/195* | (2016.01) | |
| *A61K 36/8964* | (2006.01) | |
| *A61K 36/82* | (2006.01) | |
| *A61K 36/73* | (2006.01) | |
| *A23K 50/10* | (2016.01) | |
| *A61K 36/88* | (2006.01) | |
| *A23K 20/10* | (2016.01) | |
| *A23K 10/30* | (2016.01) | |

(52) U.S. Cl.
CPC ............ *A61K 36/886* (2013.01); *A23K 10/30* (2016.05); *A23K 20/10* (2016.05); *A23K 20/158* (2016.05); *A23K 20/195* (2016.05); *A23K 50/10* (2016.05); *A61K 31/20* (2013.01); *A61K 31/215* (2013.01); *A61K 36/48* (2013.01); *A61K 36/73* (2013.01); *A61K 36/752* (2013.01); *A61K 36/77* (2013.01); *A61K 36/82* (2013.01); *A61K 36/88* (2013.01); *A61K 36/898* (2013.01); *A61K 36/8964* (2013.01); *A61K 36/8965* (2013.01); *A61P 31/04* (2018.01)

(58) Field of Classification Search
CPC ..... A23K 20/121; A23K 20/158; A23K 50/10
See application file for complete search history.

(56) References Cited

U.S. PATENT DOCUMENTS

| | | |
|---|---|---|
| 4,388,327 A | 6/1983 | Cummins |
| 5,139,779 A | 8/1992 | McNeff |
| 5,219,596 A | 6/1993 | Smith et al. |
| 5,496,571 A | 3/1996 | Blagdon et al. |
| 6,475,527 B1 | 11/2002 | Anderson et al. |
| 6,761,911 B2 | 7/2004 | Anderson et al. |
| 7,416,742 B2 | 8/2008 | McNeff et al. |
| 7,544,376 B2 | 6/2009 | McNeff et al. |
| 7,641,920 B2 | 1/2010 | Taylor, Jr. et al. |
| 8,043,633 B2 | 10/2011 | McNeff et al. |
| 2003/0039703 A1 | 2/2003 | Anderson et al. |
| 2006/0003022 A1 | 1/2006 | McNeff et al. |
| 2006/0024387 A1* | 2/2006 | McNeff ................. A61K 36/00 424/725 |
| 2006/0073194 A1 | 4/2006 | Taylor et al. |
| 2008/0274211 A1 | 11/2008 | McNeff et al. |
| 2009/0285931 A1* | 11/2009 | Shelby .................. A23K 10/30 426/2 |

FOREIGN PATENT DOCUMENTS

| | | |
|---|---|---|
| EP | 1088483 | 4/2001 |
| WO | 03056935 | 7/2003 |

OTHER PUBLICATIONS

"Sevarin® with Sarsaponin: gets 'em from feedlot to market faster, more profitably", Product Brochure, DPI Distributors Processing Inc., 1982 (4 pages).
Anderson, R. C. et al., "Effect of Sodium Chlorate on *Salmonella typhimurium* Concentrations in the Weaned Pig Gut," Journal of Food Protection, vol. 64, No. 2, pp. 255-258, 2001 (4 pages).
Asres, K. et al., "In vitro Antiprotozoal Activity of Extract and Compounds from the Stem Bark of Combretum molle," Phytotherapy Research 15, 613-617 (2001), 5 pages.
Barker, John et al., "Survival of *Escherichia coli* 0157 in a soil protozoan: implications for disease," FEMS Microbiol. Lett. 173(2), 291-295, 1999 (5 pages).
Bonyata, Kelly "How Does Milk Production Work?," Kelly's Attachment Parenting, http://web.archive.org/web/20030620083858/http://www.kellymom.com/bf/supply/milkproduction.html (Web Publication Date: Jun. 20, 2003), 5 pages.
Boyaka, Prosper N. et al., "Oral QS-21 Requires Early IL-4 Help for Induction of Mucosal and Systemic Immunity," J Immunol Feb. 15, 2001, 166 (4) 2283-2290 (8 pages).

(Continued)

*Primary Examiner* — Rosanne Kosson
(74) *Attorney, Agent, or Firm* — Pauly, DeVries Smith & Deffner LLC

(57) ABSTRACT

Embodiments herein include a composition that can include a saponin composition including saponins and at least one medium chain fatty acid (MCFA) or ester or salt thereof. In an embodiment, the saponins and at least one MCFA present in the composition can work synergistically to prevent methanogenesis by bacteria. In another embodiment, a method of processing animal feed using the compositions herein is included. Other embodiments are also included herein.

6 Claims, No Drawings

(56) References Cited

OTHER PUBLICATIONS

Brown, Sylvia et al., "The Nursing Mother's Diet," Pregnancy.org, http://web.archive.org/web/20040127064545/http://www.pregnancy.org/article.php?sid=1044 (Web Publication Date: Jan. 27, 2004), 3 pages.
Burkey, T. E. et al., "Effect of Dietary Mannanoligosaccharide and Sodium Chlorate on the Growth Performance, Acute-Phase Response, and Bacterial Shedding of Weaned Pigs Challenged with Salmonella enterica Serotype Typhimurium," J. Anim. Sci 82(2) 397-404 (Feb. 1, 2004), 8 pages.
Callaway, T. R. et al., "Sodium chlorate supplementation reduces E. coli 0157:H7 populations in cattle," J Anim Sci. Jun. 2002;80(6):1683-1689 (7 pages).
Cheeke, P. R. "Actual and Potential Applications of Yucca schidigera and Quillaja saponaria Saponins in Human and Animal Nutrition," Proceedings of the American Society of Animal Science, 1999 (10 pages).
Choat, W. T. et al., "Effect of Conventional vs. Restricted Adaptation to a High-Concentrate Diet on Performance and Carcass Characteristics of Feedlot Calves," Animal Science Research Report, 2001 (4 pages).
Dehority, Burk A. "Evaluation of Subsampling and Fixation Procedures Used for Counting Rumen Protozoa," Appl. Environ. Microbiol. 48(1), Jul. 1984, 182-185 (4 pages).
Dumitru, Razvan et al., "Targeting Methanopterin Biosynthesis to Inhibit Methanogenesis," Appl. Environ. Microbiol. 69(12), Dec. 2003, 7236-7241 (6 pages).
Eschenlauer, S. C. et al., "Ammonia Production by Ruminal Microorganisms and Enumeration, Isolation, and Characterization of Bacteria Capable of Growth on Peptides and Amino Acids from the Sheep Rumen," Appl. Environ. Microbiol. 68(10), Oct. 2002, 4925-4931 (7 pages).
Fahmy, Wael G. et al., "Effect of Defaunation and Amino Acid Supplementation on Growth and Amino Acid Balance in Sheep," http://www.traill.uiuc.edu/dairynet/paperDisplay.cfm?ContentID=238, Aug. 5, 1998 (2 pages).
"File History," for U.S. Appl. No. 11/153,252, filed Jun. 15, 2005 through Aug. 6, 2008 (220 pages).
"File History," for U.S. Appl. No. 11/193,032, filed Jul. 29, 2005 through Jul. 21, 2009 (254 pages).
"File History," for U.S. Appl. No. 11/241,237, filed Sep. 30, 2005 through Nov. 16, 2010 (136 pages).
"File History," for U.S. Appl. No. 12/175,281, filed Jul. 17, 2008 through Oct. 5, 2011 (122 pages).
Francis, George et al., "The biological action of saponins in animal systems: a review.," Br. J. Nutr. (2002), 88, 587-605 (19 pages).
Garcia-Lopez, P. M. "In Vitro Inhibition of Microbial Methane Production by 9,10-Anthraquinone," J. Anim. Sci. 1996, 74:2276-2284 (9 pages).
Goel, G. et al., "Effects of Capric Acid on Rumen Methanogenesis and Biohydrogenation of Linoleic and a-Linolenic Acid," Animal (2009), 3:6, pp. 810-816 (7 pages).
Goodall, S. R. et al., "Rumensin with and without Sarsaponin for Finishing Feedlot Steers," Col. Agr. Exp. Station 700 (1981), 4 pages.
Goodall, S. R. et al., "Sarsaponin Effects Upon Ruminal VFA Concentrations and Weight Gain of Feedlot Cattle," J. Anim. Sci. 49 (abstract only), 1979 (2 pages).
Goodall, S. R. et al., "Sarsaponin in Beef Cattle Rations," Beef Nutrition Research (1978): 9-10 (2 pages).
Goodall, S. R. et al., "The Effect of Sarsaponin with and without Rumensin in High-Energy Rations," Col. Agr. Exp. Station 700 (1981), 6 pages.
Grant, R. J. et al., "Feeding Dairy Cattle for Proper Body Condition Score," University of Missouri Agricultural Publication G3170, 1999 (5 pages).

Hoffman, D. J. et al., "The Effects of Zeranol and Munensin on Feedlot Steers," Proceedings, Western Section, American Society of Animal Science. vol. 28, 204-207 (1977), 4 pages.
Hoppe, Karl "Consequences of Underfeeding Beef Cows," http://www.ag.ndsu.edu/pubs/ansci/beef/coping/underfed.htm, 2009 (3 pages).
Hristov, A. N. et al., "Fermentation Characteristics and Ruminal Ciliate Protozoal Populations in Cattle Fed Medium- or High-Concentrate Barley-Based Diets," J. Anim. Sci. 2001. 79:515-524 (10 pages).
Hristov, Alexander N. et al., "Effect of Yucca schidigera on Ruminal Fermentation and Nutrient Digestion in Heifers," J. Anim Sci. 77(9), 2554-2563 (1999), 10 pages.
King, Christopher H. et al., "Survival of Coliforms and Bacterial Pathogens within Protozoa during Chlorination," Appl. Environ. Microbiol. 54(12), 3023-3033 (11 pages).
Klita, P. T. et al., "Effects of alfalfa root saponins on digestive function in sheep," J. Animal Sci. 74(5), 1144-1156 (13 pages).
Koenig, K. M. et al., "Effects of Protozoa on Bacterial Nitrogen Recycling in the Rumen," J. Anim Sci. 2000. 78:2431-2445 (15 pages).
Lila, Z. A. et al., "Effect of Sarsaponin on Ruminal Fermentation with Particular Reference to Methane Production in Vitro," J. Dairy Sci. 86:3330-3336 (2003), 7 pages.
Lu, C. D. et al., "Alfalfa Saponins Affect Site and Extent of Nutrient Digestion in Ruminants," J. Nutr. 17(5), 919-927 (1987), 9 pages.
Luginbuhl, J M. et al., "Forage Needs for Meat Goats and Sheep," http://web.archive.org/web/20010104120900/http://www.cals.ncsu.edu:80/an_sci/extension/animal/meatgoat/MGFrgnds.htm (Web Publication Date: Jan. 4, 2001), 6 pages.
Ly, T. M. et al., "Ingested Listeria monocytogenes Survive and Multiply in Protozoa," J. Med. Microbiol. 33(1) 1990, 51-54 (4 pages).
Maday, John "Assault on Pathogens," Drovers (www.drovers.com/news_editorial.asp?pgID=676&ed_id=2499), Feb. 12, 2004 (4 pages).
Mendoza, G. D. et al., "Influence of Ruminal Protozoa on Site and Extent of Starch Digestion and Ruminal Fermentation," J. Anim Sci. 1993. 71:1572-1578 (7 pages).
"Milk Production and Biosynthesis," University of Guelph, http://web.archive.org/web/19981202101633/http://www.foodsci.uoguelph.ca/dairyedu/biosynthesis.html (Web Publication Date: Dec. 2, 1998), 5 pages.
Miller, Terry L. et al., "Inhibition of Growth of Methane-Producing Bacteria of the Ruminant Forestomach by Hydroxymethylglutaryl-SCoA Reductase Inhibitors," J. Dairy Sci. 84(6) 1445-1448 (2001), 4 pages).
Murphy, K. D. et al., "Effects of Rearing Diet, Age at Freshening, and Lactation Feeding System on Performance," J. Dairy Sci. 74:2708-2717 (1991), 10 pages.
Navas-Camacho, Alberto et al., "Effect of Reducing the Rumen Ciliate Protozoa Population by Feeding Saponin-Containing Plants on Rumen Function of Sheep Fed on Wheat Straw," Arch. Latinoam. Prod. Anim. 5(Supl. 1): 98-101 (1997), 4 pages.
Oldick, B. S. et al., "Compartmental Modeling with Nitrogen-15 to Determine Effects of Degree of Fat Saturation on Intraruminal N Recycling," J. Anim. Sci. 2000. 78:2421-2430 (10 pages).
Oldick, B. S. et al., "Effects of Degree of Fat Saturation on Fiber Digestion and Microbial Protein Syntehsis when Diets are Fed Twelve Times Daily," J. Anim. Sci. 2000. 78:2412-2420 (9 pages).
Rasmussen, M. A. "Microbial Factors/Pathogenesis of Subacute Rumen Acidosis (SARA) in Cattle to Assure Food Safety," Project No. 3625-31320-001-00D, National Animal Disease Center, ARS/USDA, 2005 (1 page).
Rasmussen, Mark A. et al., "Escherichia coli 0157:H7 and the Rumen Environment," E. coli O157 in Farm Animals (CAB International 1999), 11 pages., 39-49.
Rush, Ivan et al., "Grain Tempering Agent (SarTemp) for Corn in Finishing Rations," Beef Cattle Report (1993): 63-64 (3 pages).
Taylor, Stephanie J. et al., "Infection of Acanthamoeba castellanii with Mycobacterium bovis and M. bovis BCG and Survival of M. bovis within the Amoebae," Appl. Environ. Microbiol. 69(7), 4316-4319, 2003 (4 pages).
Towne, Gene et al., "Omasal Ciliated Protozoa in Cattle, Bison, and Sheep," Appl. Environ. Microbiol. 56(2), 409-412 (1990), 4 pages.

(56) References Cited

OTHER PUBLICATIONS

Uematsu, Yoko et al., "Spectrophotometric Determination of Saponin in Yucca Extract Used as Food Additive," Journal of AOAC International 83(6), 1451-1454 (2000), 4 pages. http://www.extenza-eps.com/AOAC/doi/abs/10.5555/jaoi.2000.83.6.1451;jsessionid=o58x-ptaAnThldpNjT?cookieSet=1&journalCode=jaoi (Date Accessed: May 15, 2006).

Valdez, F. R. et al., "Effect of Steroidal Sapogenins on Ruminal Fermentation and on Production of Lactating Dairy Cows," J. Dairy Sci. 69(6), 1568-1575 (1986), 8 pages.

Wallace, R. J. "Influence of Yucca Shidigera Extract on Ruminal Ammonia Concentrations and Ruminal Microorganisms," Appl. Environ. Microbiol. 60(6), 1762-1767 (1994), 6 pages.

Wang, Y. et al., "Effect of Steroidal Saponin from Yucca schidigera Extract on Ruminal Microbes," J. Appl. Microbiol. 88(5), 887-896 (2000), 10 pages.

Wang, Y. et al., "Effects of Yucca Schidigera extract on fermentation and degradation of steroidal sponins in the rumen simulation technique (RUSITEC)," Animal Feed Sci. Technol. 74(2), 143-153 (1998), 11 pages.

Wattiaux, Michel A. et al., "Chapter 1: Digestion in the Dairy Cow," The Babcock Institute for International Dairy Research and Development—The University of Wisconsin Madison. http://babcock.wisc.edu/downloads/de_html/ch01.en.html, 2007 (4 pages).

Wilson, R. C. et al., "Effects of Yucca shidigera Extract and Soluble Protein on Performance of Cows and Concentrations of Urea Nitrogen in Plasma and Milk," J. Dairy Sci. 81(4), 1022-1027 (1998), 6 pages.

Zinn, R. A. et al., "Influence of tempering on the feeding value of rolled corn in finishing diets for feedlot cattle," J. Anim Sci. 76(9), 2239-2246 (1998), 8 pages.

* cited by examiner

COMPOSITIONS AND METHODS FOR MITIGATING METHANOGENESIS IN ANIMALS

This application claims the benefit of U.S. Provisional Application No. 62/506,726, filed May 16, 2017, the content of which is herein incorporated by reference in its entirety.

FIELD

Embodiments herein relate to compositions including saponins and medium chain fatty acids, and methods for using the same. In particular, the invention is related to compositions including saponins and medium chain fatty acids useful for mitigating methanogenesis in animals.

BACKGROUND

According to the Environmental Protection Agency, methane gas emitted by ruminant animals accounted for around 10% of all greenhouse gas emissions in the U.S in 2015. Reduction of methane gas-producing bacteria, called methanogens, in ruminant animals is not only important for reducing the total amount of methane gas emitted into the environment, but it is also important because the production of methane gas in the rumen is often carried out at the nutrient-expense of these animals.

SUMMARY

Embodiments herein relate to compositions including saponins and medium chain fatty acids or esters or salts thereof, and methods for using the same. In particular, the invention is related to compositions including saponins and medium chain fatty acids useful for mitigating methanogenesis in animals.

In an embodiment, a composition is included herein. The composition can include a saponin composition including saponins and at least one medium chain fatty acid (MCFA) or ester or salt thereof. The saponins and at least one MCFA work synergistically to prevent methanogenesis by bacteria.

In an embodiment, a method of processing animal feed is included. The method can include contacting an animal feed material with a composition, the composition including a saponin composition comprising saponins and at least one MCFA or ester or salt thereof. The at least one medium chain fatty acid prevents methanogenesis by bacteria.

In an embodiment, a method of treating an animal to reduce methanogensis is included. The method can include administering an effective dose of a composition to the animal. The composition can include a saponin composition comprising saponins and at least one medium chain fatty acid or ester or salt thereof. The saponins and at least one MCFA can prevent or reduce methanogenesis by bacteria within the animal.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

DETAILED DESCRIPTION

It is known that methanogenic bacteria living in the rumen of some animals produce methane gas through a process called methanogenesis. In addition, ruminal protozoa have been shown to produce hydrogen in the rumen, which is utilized by the methanogens to produce methane. Saponins and medium chain fatty acids (MCFAs) are versatile molecules with many different applications. Saponins and MCFAs, described more fully below, have various beneficial dietary properties when fed to animals and in particular with respect to their effects on reducing methanogensis.

Compositions used with the embodiments herein, can include saponins in various combinations with MCFAs. In some embodiments, compositions included herein can be mixed in with animal feed material. In this manner, the composition can act as a feed conditioning agent. Therefore, in an embodiment, the invention includes a feed conditioning composition including a saponin composition comprising saponins and at least MCFA that can work synergistically to prevent methanogenesis by bacteria.

Compositions included with embodiments herein can be formulated in various ways. For example compositions herein can be formulated as a liquid, slurry, dry powder, dry granular mix, paste, pellets, block, or the like. Compositions may be administered to an animal as a pill, a bolus, or a liquid drench.

In accordance with embodiments included herein, compositions including a saponin composition comprising saponins and one or more MCFAs can be administered to an animal along with the animal's feed ration. For example, a composition, such as a liquid or solid composition can be mixed in with an animal's feed ration. In some embodiments, a composition, such as a liquid composition, can be mixed in with an animal's water.

Saponins

Various compositions herein can include saponins and/or saponin compositions. Saponins are natural plant surfactants that occur in over 500 different plant species belonging to some 80 different families. They are generally recognized by their strong foaming action when placed in water, which has made them especially useful in the manufacture of foods, beverages, shampoos, wetting agents and pharmaceuticals.

Saponins are classified as surfactants because they have both lipophilic and hydrophilic "regions." Thus, the surfactant activity of saponins is a result of both fat-soluble and water-soluble moieties in the same molecule. The lipophilic region may be a steroid, triterpene, or alkaloid, and is termed a sapogenin. The hydrophilic "region" contains one or more water-soluble carbohydrate side chains. The structural complexity of saponins is derived largely from the carbohydrate portion of the molecule due to the many different types of possible side chain carbohydrates, such as glucose, xylose, galactose, pentose or methylpentose, which may have different connectivity and/or anomeric configuration.

Saponins can play a role in reducing or eliminating ruminal protozoa. Saponins (triterpenoid, steroidal, or alkaloid) have a hemolytic action that is believed to be related to their affinity for cell membrane sterols that are embedded in the lipid bi-layer, and in particular cholesterol. Saponins have been shown to form insoluble complexes with cholesterol and thereby open holes in cell membranes of ruminal protozoa to cause cell lysis. The ability of saponins to rupture cell membranes, but yet be non-toxic to mammals when ingested orally makes them a suitable protozoan eliminator for use in livestock.

Saponins useful in the present invention can be extracted from plants of the family: Lillaecae, genus: *Yucca*, such as *Yucca schidigera*. *Yucca* derived saponins generally have steroidal sapogenins. Sarsasapogenin is the major sapogenin found in the *Yucca schidigera* plant. Saponins useful in the present invention can also be extracted from plants of the family: Amaryllidaccae, genus: *Agave,* which grows extensively in the southwestern United States and Mexico. Additional sources of saponins can include extracts of soybeans, fenugreek, peas, tea, yams, sugar beets, *alfalfa,* asparagus, *aloe,* vanilla, zhimu, *Sapindus saponaria,* citrus fruits (limonoid saponins) as well as from *Quillaja saponaria* bark.

The typical saponin content that naturally occurs in *Yucca* plants is from 0.1-2% saponins by weight. *Yucca* extracts can be derived by extracting *yucca* powder with an aqueous solution that may or may not contain some fraction of organic solvent such as methanol, ethanol, propanol, butanol, or the like.

Commercially available *Yucca* extracts can have total solids content usually in the range from 5-50% solids by weight. The saponin content of a typical 50 brix (50% solids by weight) *yucca* extract is usually in the range of about 1-2% saponins by weight as measured by HPLC analysis. Another method of measuring total saponin content is the extraction of all soluble components into a butanol extract followed by gravimetric analysis of the compounds dissolved in the butanol fraction. Measuring saponin content by the butanol extract method typically results in higher numbers than the more advanced HPLC method. Accordingly, the typical 50 brix (50% solids by weight) *yucca* extract is usually in the range of about 5-20% saponins content by weight as measured by the butanol extract method.

In an embodiment, the composition can include at least 0.1% by weight saponins as measured by HPLC. In an embodiment, the composition can include at least 0.5% by weight saponins as measured by HPLC. In an embodiment, the composition can include at least 1.0% by weight saponins as measured by HPLC. In an embodiment, the composition can include at least 2.0% by weight saponins as measured by HPLC. In an embodiment, the composition can include at least 5.0% by weight saponins as measured by HPLC. In an embodiment, the composition can include at least 7.5% by weight saponins as measured by HPLC. In an embodiment, the composition can include at least 10.0% by weight saponins as measured by HPLC.

Medium Chain Fatty Acids

Compositions used with the embodiments herein can include a medium chain fatty acid (MCFAs) and/or salts and/or esters thereof. MCFAs are fatty acids with aliphatic tails having 6 to 12 carbon atoms. Exemplary MCFAs can include caproic acid (C6:0—carbon number in fatty acid chain:number of double bonds in fatty acid chain), caprylic acid (C8:0), capric acid (C10:0), and lauric acid (C12:0). Additional MCFAs can include enanthic acid (C7:0), pelargonic acid (C9:0), and undecylic acid (C11:0). MCFAs in their salt (including, but not limited to, sodium, potassium, calcium, magnesium, zinc, aluminum, ammonium, iron, pyridinium, and the like) and ester forms (including, but not limited to, alkyl, C1 to C8 alkyl, methyl, ethyl, propyl, butyl, aryl, C4 to C30 aryl, and the like) are also suitable for use in the compositions described herein. Other suitable MCFAs can include straight chain, unbranched fatty acids or branched fatty acids, and those that are saturated or unsaturated. MCFAs in accordance with the embodiments herein can also exist as a component of a mono-, di-, and triglyceride.

In some embodiments, any combination of caproic, caprylic, capric, and lauric acids can be used in accordance with the compositions herein. In some embodiments, the compositions herein can include caproic acid. In some embodiments, the compositions herein can include capryilic acid. In some embodiments, the compositions herein can include capric acid. In some embodiments, the compositions herein can include lauric acid.

MCFAs can be useful antimicrobial agents when incorporated into the diet of animals. Without being bound by theory, it is believed that MCFAs remain in their undissociated form in the low to neutral pH of the stomach or rumen of animals. Undissociated MCFAs can penetrate the phospholipid bilayer of bacterial cells present in the stomach or rumen, where they become concentrated within the cytoplasm of the bacterial cells. Once inside the cell, MCFAs can be degraded within the cytoplasm resulting in acidification of the cell and eventually leading to cell death. As such, it is believed that MCFAs can play a key role in reducing or eliminating ruminal methanogens.

MCFAs have additional implications for enhancing energy utilization by the animals. The enzymatic degradation of dietary essential fatty acids by bacteria present in the rumen can lead to a decrease in the availability of dietary energy present in feed material. For example, the essential fatty acids, linoleic acid (C18:2) and linolenic acid (C18:3), can be cleaved from dietary sources of di- or tri-glycerides by bacterial enzymes present in the stomach or rumen through the process of lipolysis. Breakdown of di- and tri-glycerides leads to the formation of glycerol and free fatty acids. Following lipolysis, the free fatty acids of linoleic acid and linolenic acid can be further degraded by the bacterial enzymes isomerase and reductase, through the process of biohydrogenation, into other non-essential fatty acids such as stearic acid (C18:0). The degradation of essential fatty acids can include a decrease from 70-90% by weight the original amount present in an animal feed. Thus, the available essential fatty acids in the animal's diet is reduced significantly.

Use of saponins in combination with MCFAs can significantly reduce the number of protozoal and methanogenic bacteria in the rumen, resulting in a decrease in both hydrogen and methane gas formation. One benefit of adding the combination of saponins and MCFAs to the diet of animals is the increase of available essential free fatty acids to the animal once the digested material reaches the small intestine. Another benefit of adding both saponins and MCFAs into the diet of animals is that the antibacterial effects of the compositions help reduce the dependence on antibiotic supplementation, which helps mitigate antibiotic resistance.

In accordance with the embodiments herein, saponins and the MCFAs can be included in a composition in a molar ratio of 1:20 to 20:1. The saponins and the MCFAs can be in a molar ratio of 1:4 to 4:1. In some embodiments, the saponins and the MCFAs can be in a molar ratio of about 1:1. The saponins and the MCFAs can be in a weight ratio of about 10:1 to 30:1.

In some embodiments, the composition can include at least about 0.1, 0.5, 1.0, 2.0, 4.0, 6.0, 8.0, 10, 15 or 20% by weight of the MCFAs. In some embodiments the composition can include less than about 25, 20, 15, 10, 8.0, 5.0 or 2.0% by weight of the MCFAs. In some embodiments, the amount of the MCFAs can be in a range wherein any of the foregoing numbers can serve as the upper or lower bound of the range.

Animal Feed Materials

In an embodiment, the invention includes a method of processing animal feed including contacting an animal feed material with a composition including a saponin and at least one MCFA. By adding the composition to the animal feed, dosing can be simplified as the composition will reach the rumen along with the feed.

It will be appreciated that animal feed materials can include many different components such as, but not limited to, *alfalfa* hay, *alfalfa* haylage, almond hulls, apple components, rolled barley, barley malt sprouts, barley silage, bermuda grass, blood meal, bluegrass, brome, canary grass, canola seed, canola meal, chocolate byproduct, dried citrus pulp, clover, sudangrass hay, dry-rolled corn, tempered-rolled corn, steam-flaked corn, ground shelled corn, cracked corn, hominy feed, corn gluten feed, corn silage, wet brewer's grain, dry brewer's grain, distillers grains (dried and wet), stillage, soybean meal, soybean seeds, soybean hulls, sunflower meal, sunflower oil, sunflower seeds, tomato products, wheat bran, rolled wheat, wheat hay, wheat middlings, wheat silage, whey, fescue, fish byproducts, hay, legumes, linseed, meat meal, meat and bone meal, rolled oats, oat hay, oat silage, orchard grass, peanut meal, potato byproduct meal, rice bran, rye, safflower, dry rolled sorghum, steam-flaked sorghum, sorghum silage, soybean hulls, whole cottonseed, cottonseed hulls, cottonseed meal, sugar beet pulp, dehydrated beet pulp, bakery waste, cottonseed meal, yellow grease, white grease, vegetable oil, palm oil, coconut oil, cottonseed oil, sunflower oil, flax seed oil, safflower oil, corn oil, soybean oil, sesame oil, canola oil, olive oil, tallow, water, hydrolyzed feather meal, cane molasses, sugar beet molasses, and the like, and combinations thereof.

It will be appreciated that feed materials high in MCFAs, including but not limited to palm kernel oil and coconut oil, can be suitable for use in the compositions herein. Additionally, mixtures of feed materials high in MCFAs, including but not limited to palm kernel oil and coconut oil, can be suitable for use in the compositions herein.

In some embodiments, the animal feed material can specifically include byproducts of ethanol production. For example in some embodiments, the animal feed material can specifically include distillers dried grains, distillers wet grains, and/or stillage.

It will be appreciated that methods and compositions of the invention can be used for the treatment of animals, including bovine, fowl, porcine, ovine, and equine species. By way of example, the methods and compositions of the invention can be used for the treatment of cattle, chickens, turkeys, ducks, quail, geese, pigs, and sheep. In a specific embodiment, the methods and compositions of the invention can be used for the treatment of ruminants.

In an embodiment, a method of treating an animal to reduce methanogensis is included. The method can include administering an effective dose of a composition to the animal. The composition can include a saponin composition comprising saponins and at least one medium chain fatty acid. The saponins and at least one MCFA can prevent or reduce methanogenesis by bacteria within the animal.

In some embodiments the method can further include selecting an animal exhibiting signs of elevated methanogenesis. In some embodiments the animal can be a ruminant. In some embodiments the animal can be *Bos taurus*.

It will be appreciated that compositions in accordance with embodiments herein can include various additives. By way of example, compositions can also include additives such as water, propylene glycol, Vitamin E (as di-alpha-tocopheryl acetate), Vitamin A Propionate, Vitamin A Palmitate, Vitamin B1, Vitamin B2, Vitamin B6, Vitamin B12, D-Activated Animal Sterol (source of Vitamin D3), yeast components, dried egg solids, dried casein, and dried whey, amongst others.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein. As such, the embodiments described herein are not intended to be exhaustive or to limit the invention to the precise forms disclosed in the following detailed description. Rather, the embodiments are chosen and described so that others skilled in the art can appreciate and understand the principles and practices.

The invention claimed is:

1. A method of treating an animal feed to decrease methanogenesis resulting from consumption of the feed by an animal, comprising: contacting the animal feed with an effective amount of a composition, the composition comprising:
   (a) a plant extract comprising saponins; and
   (b) at least one medium chain fatty acid (MCFA), or ester or salt thereof; wherein the saponins and the at least one MCFA, or ester or salt thereof decrease methanogenesis by bacteria in the animal that consumes the feed.

2. The method of claim 1, wherein the plant extract is a *Yucca* extract.

3. The method of claim 1, the at least one (MCFA), or ester or salt thereof comprising caproic acid, caprylic acid, capric acid, or lauric acid.

4. The method of claim 1, the at least one (MCFA), or ester or salt thereof comprising capric acid.

5. The method of claim 1, wherein the saponins and the at least one MCFA, or ester or salt thereof are in a molar ratio of 1:20 to 20:1.

6. The method of claim 1, wherein the saponins and the at least one MCFA, or ester or salt thereof are in a molar ratio of 1:4 to 4:1.

* * * * *